(12) United States Patent
Bruce et al.

(10) Patent No.: US 10,413,002 B2
(45) Date of Patent: *Sep. 17, 2019

(54) GLOVES WITH A CUT OUT PORTION AND METHODS TO MANUFACTURE GLOVES WITH A CUT OUT PORTION

(71) Applicant: Karsten Manufacturing Corporation, Phoenix, AZ (US)

(72) Inventors: Ryan J. Bruce, Phoenix, AZ (US); John H. Loudenslager, Phoenix, AZ (US); Toby Stapleton, Loughborough (GB)

(73) Assignee: Karsten Manufacturing Corporation, Phoenix, AZ (US)

( * ) Notice: Subject to any disclaimer, the term of this patent is extended or adjusted under 35 U.S.C. 154(b) by 46 days.

This patent is subject to a terminal disclaimer.

(21) Appl. No.: 15/383,075

(22) Filed: Dec. 19, 2016

(65) Prior Publication Data
US 2017/0095018 A1    Apr. 6, 2017

Related U.S. Application Data

(63) Continuation-in-part of application No. 15/264,969, filed on Sep. 14, 2016, which is a continuation of
(Continued)

(51) Int. Cl.
*A41D 19/00* (2006.01)
*A63B 71/14* (2006.01)
(Continued)

(52) U.S. Cl.
CPC ..... *A41D 19/0013* (2013.01); *A41D 19/0017* (2013.01); *A41D 19/0044* (2013.01);
(Continued)

(58) Field of Classification Search
CPC ............ A41D 19/0017; A41D 19/0013; A41D 19/0044; A63B 71/143; A63B 71/145;
(Continued)

(56) References Cited

U.S. PATENT DOCUMENTS 1,519,913 A * 12/1924 Hynes ................ A41D 19/0055
2/158
1,578,127 A * 3/1926 Hynes ................ A41D 19/0055
2/158
(Continued)

FOREIGN PATENT DOCUMENTS

| CN | 2308415 Y | 2/1999 |
|---|---|---|
| CN | 201509664 U | 6/2010 |
| GB | 2316855 | 3/1998 |

OTHER PUBLICATIONS

International Search Report and Written Opinion for corresponding International Application No. PCT/US2014/045568 dated Jul. 8, 2015. 10 pages.
(Continued)

*Primary Examiner* — Shaun R Hurley
*Assistant Examiner* — Bao-Thieu L Nguyen

(57) ABSTRACT

Embodiments of a glove including a cut out portion and a reinforcing panel are described herein. In many embodiments, a glove comprises a glove body with a dorsal side, a palmar side, a plurality of finger portions, a thumb portion, and a wrist portion. The wrist portion defines a glove opening in communication with an interior portion defined within the glove body. A reinforcing panel is secured on an outer surface of the glove body between the thumb portion and the wrist portion. A cut out portion defines an opening formed through the reinforcing panel and in communication with the interior portion of the glove body to minimize bunching up of the glove body. Other embodiments of gloves are described herein.

17 Claims, 15 Drawing Sheets

Related U.S. Application Data application No. 14/297,340, filed on Jun. 5, 2014, now Pat. No. 9,456,643, which is a continuation-in-part of application No. 13/949,421, filed on Jul. 24, 2013, now Pat. No. 9,211,468.

(60) Provisional application No. 62/270,128, filed on Dec. 21, 2015.

(51) Int. Cl.

| | | |
|---|---|---|
| *A41D 19/015* | (2006.01) | |
| *A61B 42/10* | (2016.01) | |
| *A63B 102/24* | (2015.01) | |
| *A63B 102/32* | (2015.01) | |
| *A63B 102/20* | (2015.01) | |
| *A63B 102/14* | (2015.01) | |
| *A63B 102/18* | (2015.01) | |

(52) U.S. Cl.
CPC .. *A41D 19/01511* (2013.01); *A41D 19/01523* (2013.01); *A61B 42/10* (2016.02); *A63B 71/141* (2013.01); *A63B 71/143* (2013.01); *A63B 71/145* (2013.01); *A63B 71/146* (2013.01); *A63B 71/148* (2013.01); *A41D 2400/44* (2013.01); *A41D 2600/104* (2013.01); *A41D 2600/202* (2013.01); *A63B 2102/14* (2015.10); *A63B 2102/18* (2015.10); *A63B 2102/20* (2015.10); *A63B 2102/24* (2015.10); *A63B 2102/32* (2015.10); *A63B 2243/002* (2013.01); *A63B 2244/04* (2013.01); *A63B 2244/09* (2013.01); *A63B 2244/10* (2013.01); *A63B 2244/19* (2013.01); *A63B 2244/24* (2013.01)

(58) Field of Classification Search
CPC . A63B 71/146; A63B 71/148; A63B 2244/04; A63B 2244/002; A63B 2244/09; A63B 2244/19; A63B 2244/24
See application file for complete search history.

(56) References Cited

U.S. PATENT DOCUMENTS

| | | | |
|---|---|---|---|
| 1,716,221 A | | 2/1928 | Fernie |
| 2,270,363 A | * | 1/1942 | Weeber ............... A41F 1/06 2/159 |
| 2,907,047 A | | 4/1959 | Steinberg |
| 3,649,966 A | * | 3/1972 | Shields ............ A41D 19/01535 2/159 |
| 3,890,649 A | * | 6/1975 | Diggins ............... A63B 71/148 2/16 |
| 5,020,160 A | | 6/1991 | Cano |
| 5,513,391 A | * | 5/1996 | Garneau ................. A41F 1/06 2/160 |
| 5,575,005 A | * | 11/1996 | Walker ................. A63B 71/143 2/161.1 |
| 6,122,769 A | | 9/2000 | Wilder |
| 6,223,354 B1 | * | 5/2001 | Carothers ............ A63B 71/146 2/161.2 |
| 6,732,377 B1 | * | 5/2004 | Wilkinson ....... A41D 19/01552 2/161.4 |
| 6,912,731 B2 | * | 7/2005 | Cass ................. A41D 19/01564 2/160 |
| 7,275,267 B2 | * | 10/2007 | Thiruppathi ......... A41D 13/088 2/160 |
| 7,284,546 B2 | | 10/2007 | Maki |
| 7,480,944 B2 | * | 1/2009 | Nascimento ............. A41F 1/06 2/159 |
| 7,761,931 B2 | | 7/2010 | Schrodl |
| 7,836,839 B2 | * | 11/2010 | Park ................... A41D 19/0068 112/475.09 |
| RE42,895 E | * | 11/2011 | Thiruppathi ......... A41D 13/088 2/160 |
| D656,684 S | * | 3/2012 | Carroll ..................... D29/117.1 |
| 9,211,468 B2 | * | 12/2015 | Bruce ................. A63B 71/146 |
| 9,456,643 B2 | * | 10/2016 | Bruce ................. A63B 71/141 |
| 2004/0216216 A1 | * | 11/2004 | Terris .............. A41D 19/01523 2/161.2 |
| 2007/0150999 A1 | | 7/2007 | Brown |
| 2011/0047670 A1 | * | 3/2011 | Anderson ................ A41F 1/06 2/161.1 |
| 2011/0113527 A1 | * | 5/2011 | Chen ................. A41D 19/0157 2/160 |
| 2013/0025023 A1 | * | 1/2013 | Anthony ................ A41D 19/01 2/158 |
| 2015/0026865 A1 | | 1/2015 | Bruce et al. |
| 2017/0000200 A1 | * | 1/2017 | Bruce ................. A63B 71/141 |
| 2017/0095018 A1 | * | 4/2017 | Bruce ................. A41D 19/0013 |

OTHER PUBLICATIONS

Written Opinion as dated Feb. 4, 2016 in corresponding PCT Application No. PCT/US2014/045568. 6 pages.

\* cited by examiner

GLOVES WITH A CUT OUT PORTION AND METHODS TO MANUFACTURE GLOVES WITH A CUT OUT PORTION

CROSS-REFERENCE TO RELATED APPLICATIONS

This claims the benefit of U.S. Provisional Patent Application No. 62/270,128, filed on Dec. 21, 2015, and is a continuation in part of U.S. patent application Ser. No. 15/246,969, filed on Sep. 14, 2016, which is a continuation of U.S. patent application Ser. No. 14/297,340, filed on Jun. 5, 2014, and issued as U.S. Pat No. 9,456,643, which is a continuation in part of U.S. patent application Ser. No. 13/949,421, filed on Jul. 24, 2013, and issued as U.S. Pat No. 9,211,468, all of which are incorporated herein by reference in their entirety.

FIELD

The present document generally relates to gloves, and in particular to gloves with a cut out portion defining an opening that substantially minimizes the bunching up of glove material during use and also provides a surface area that enables individuals to pull such gloves over their hands more efficiently.

BACKGROUND

Gloves are typically used to provide a surface area surrounding the hand that allows an individual to securely grasp and handle various types of articles or objects. For example, golf gloves are used to securely grasp a golf club when swinging or otherwise handling the golf club. Many individuals prefer that the golf glove fit snuggly around the hand which requires the cumbersome task of working the digits of the hand into the tight-fitting confines of the golf glove; however, individuals with arthritic hands may have a difficult time in effectively working the hand into the tight-fitting confines of the golf glove. In addition, the glove material of some golf gloves may bunch up in the area between the wrist portion and thumb portion when the wrist of an individual is in a hinged position during the golf swing, which may be uncomfortable to the individual. Moreover, golf gloves may also develop a failure zone in this area over a period of time due to repeated use that may cause the glove material to wear out and tear.

DESCRIPTION

Figure 1:
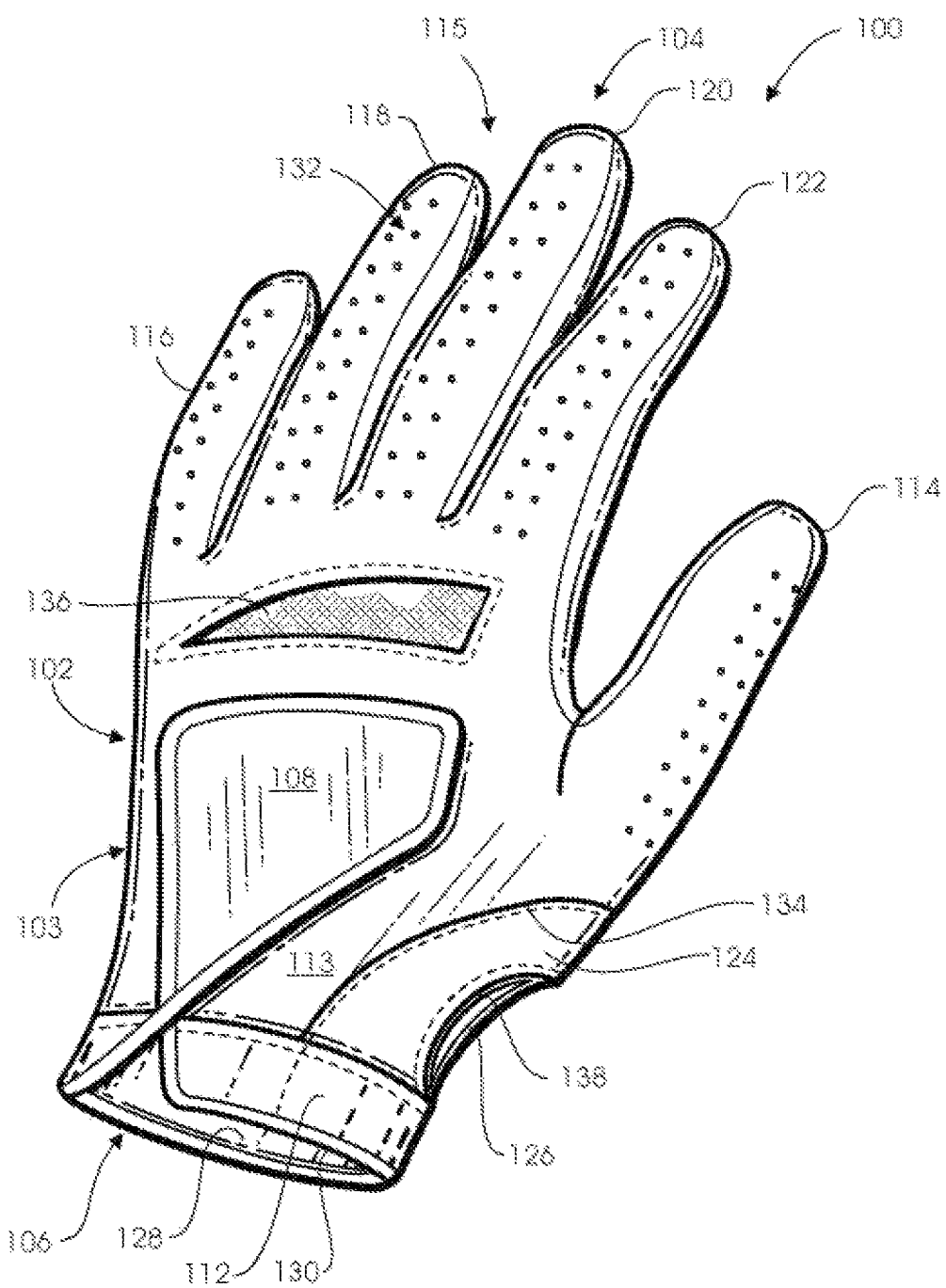
FIG. 1 is a perspective view of one embodiment of a glove showing a reinforcing panel defining a cut out portion.

Gloves with a cut out portion and methods of manufacturing such gloves to prevent bunching up of glove material and also enable an individual to more effectively pull such gloves over the hand are described herein. As used herein, the term "bunching up" refers to the gathering together of glove material in substantially one or more areas of the glove body, for example, by folding, twisting and/or bending of the glove material. Referring to the drawings, embodiments of gloves are illustrated and generally indicated as 100, 200, 300, 400, 500 and 600 in FIGS. 1-14.

Figure 2:
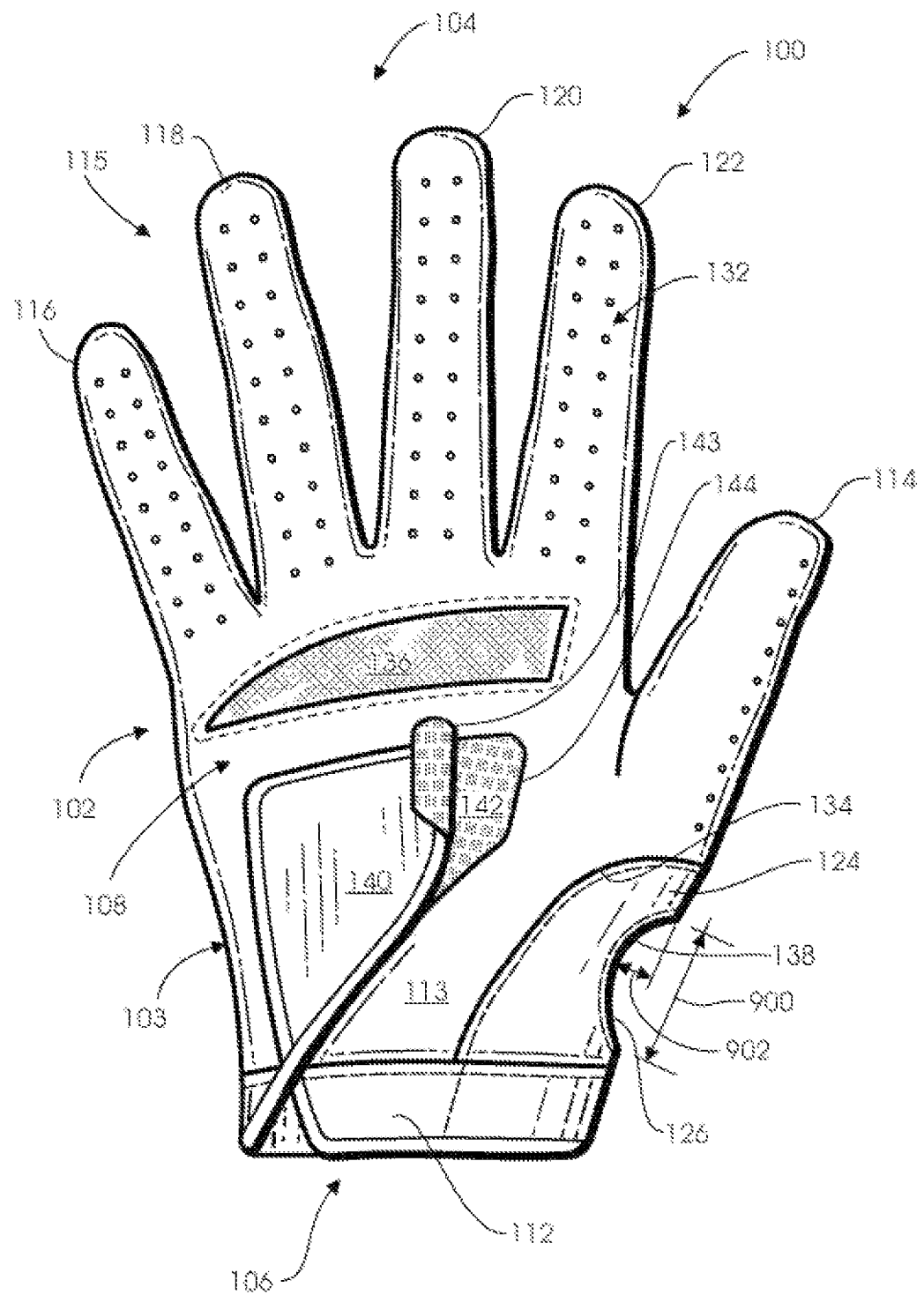
FIG. 2 is a front view of the glove of FIG. 1 showing the dorsal side of the glove.
Figure 3:
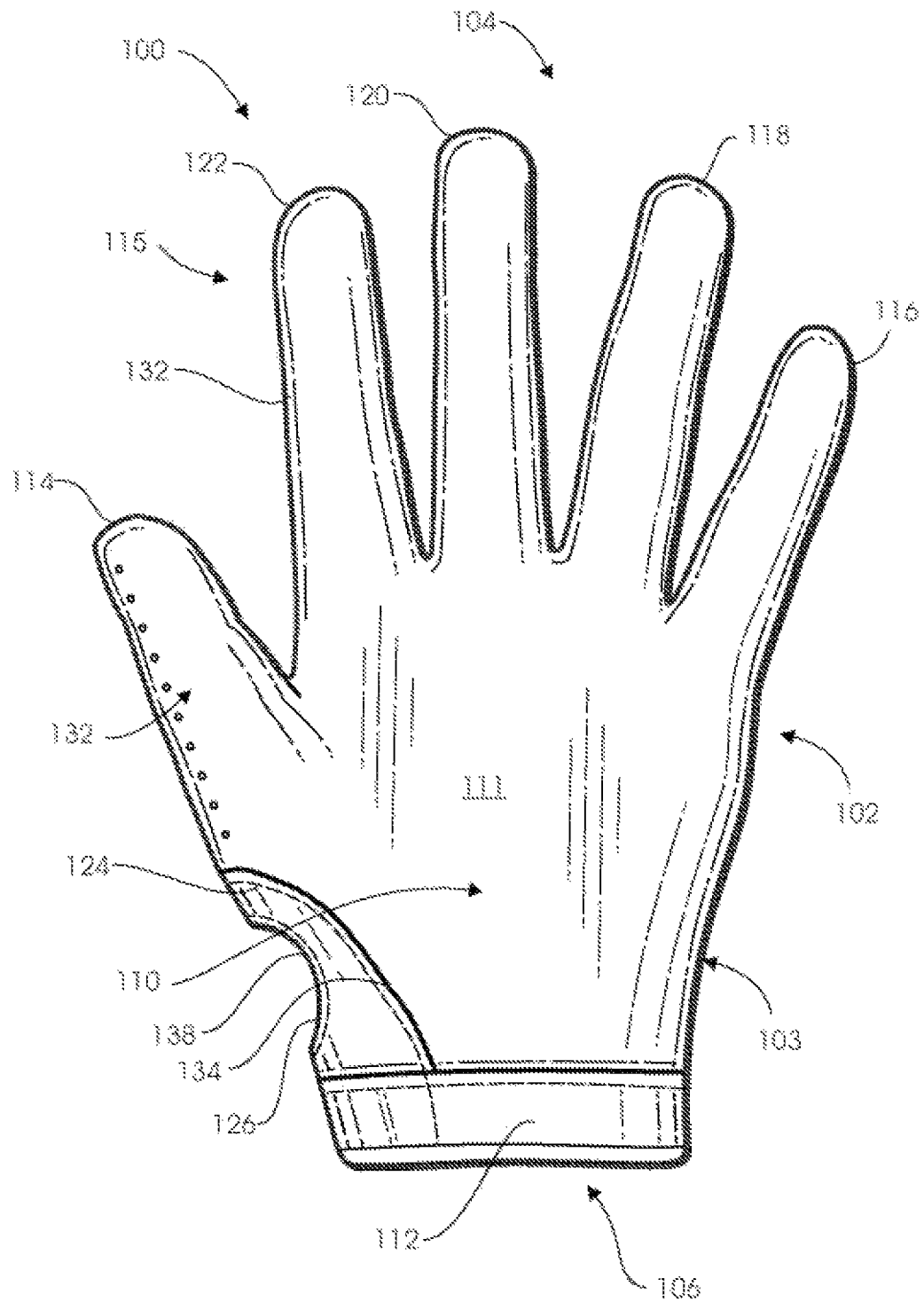
FIG. 3 is a rear view of the glove of FIG. 1 showing the palmar side of the glove.

As shown in FIGS. 1-3, one embodiment of the glove, generally designated 100, may include a glove body 102 made of a glove material 103 having a dorsal side 108 (FIGS. 1 and 2) configured to contact the backside of an individual's hand and a palmar side 110 (FIG. 3) configured to contact the palm of an individual's hand. In addition, the glove body 102 defines a first end 104 in which a plurality of finger portions 115 and a thumb portion 114 extend outwardly and a second end 106 that defines a wrist portion 112 defining a glove opening 128 (FIG. 1) configured to receive a wrist of an individual. In one embodiment, the plurality of finger portions 115 includes a first finger portion 116 configured to receive the pinky finger of an individual, a second finger portion 118 configured to receive the ring finger of an individual, a third finger portion 120 configured to receive middle finger of an individual, and a fourth finger portion 122 configured to receive the index finger of an individual when the individual pulls the glove 100 on over the hand. In one embodi10310ment, the glove body 102 may be configured for a right-handed individual, while in another embodiment the glove body 102 may be configured for a left-handed individual.

In some embodiments, the wrist portion 112 may include an elastic band (not shown) around the periphery of the wrist portion 112 that allows the wrist portion 112 to fit snugly around an individual's wrist after the glove 100 has been put on by the individual. As further shown FIG. 1, the glove opening 128 is in communication with an interior portion 130 of the glove body 102 configured to receive an individual's hand therein when the individual pulls on the glove 100.

Figure 4:
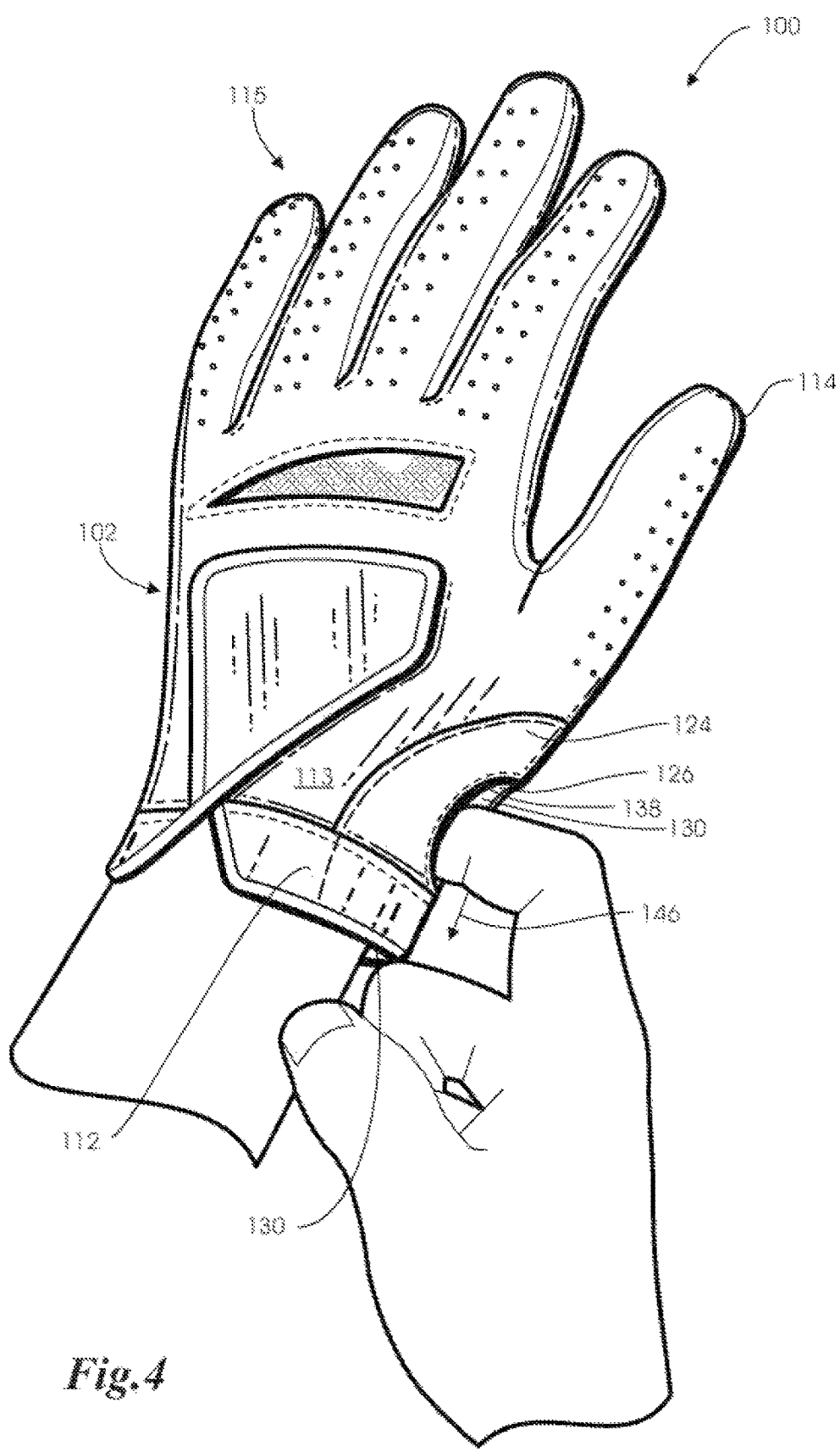
FIG. 4 is perspective view of the golf glove of FIG. 1 showing an individual engaging the cut out portion with their finger when putting on the glove over the hand.

In one embodiment, the glove body 102 may include a reinforcing panel 124 defining the cut out portion 126 having an opening 138 configured to provide a grasping surface for an individual to engage with one or more fingers when pulling on or off the glove 100 as shown in FIG. 4. The opening 138 is formed through the material of the reinforcing panel 124 and is in communication with the interior portion 130 of the glove body 102. In some embodiments, the reinforcing panel 124 may be made of a durable, resilient material, such as a leather material, a flexible soft touch polymer material, a woven material, or a variety of other synthetic textiles, suitable for repeated pulling, tugging, and/or grasping by an individual without showing any substantial wear. In one embodiment, the reinforcing panel 124 may be located between the thumb portion 114 and the wrist portion 112 that spans across both the dorsal side 108 and the palmar side 110 of the glove body 102. In other embodiments, the reinforcing panel 124 may be located between the first finger portion 116 and the wrist portion 112, or located only on the palm portion 111 adjacent the wrist portion 112 of the glove body 102, or located only on the dorsal portion 113 adjacent the wrist portion 112 of the glove body 102. While the examples may describe particular locations for the reinforcing panel 124 along the glove body 102, the apparatus, methods, and articles of manufacture described herein are not limited in this regard.

Figure 7:
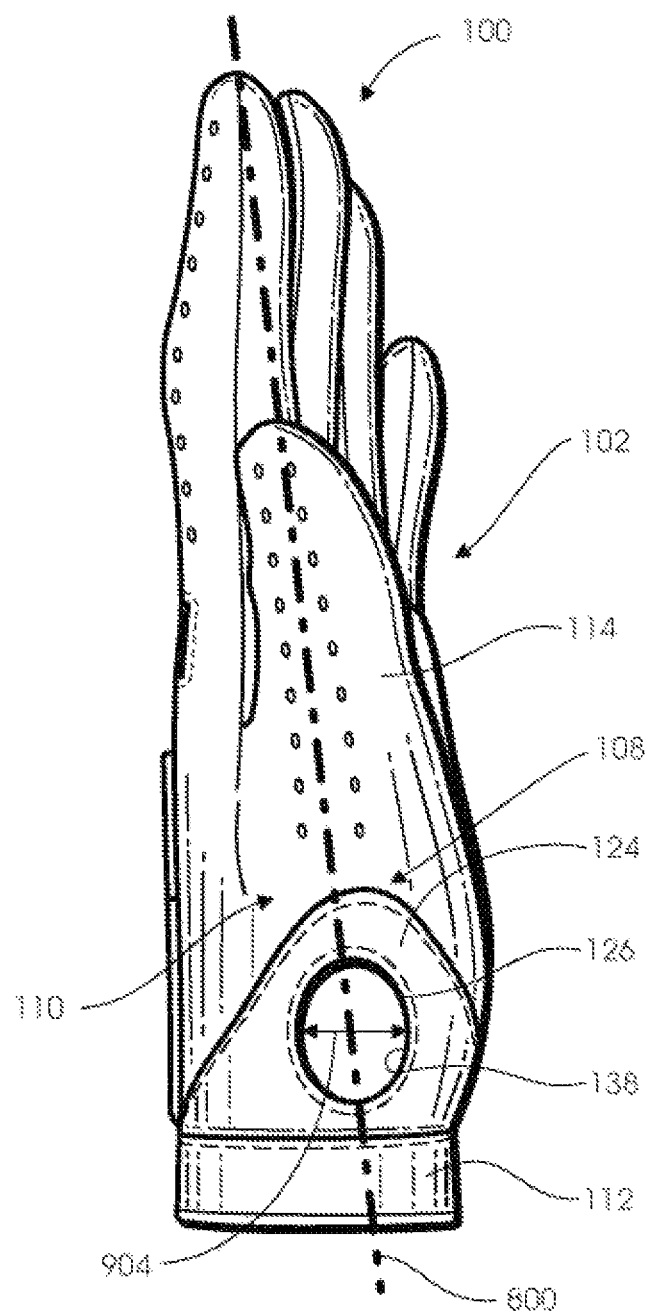
FIG. 7 is a side view of the glove of FIG. 1 showing the cut out portion having a substantially oval-shaped configuration.

In the embodiment of the glove 100 shown in FIG. 7, the opening 138 of the cut out portion 126 may be formed by removing substantially equal portions of material from the dorsal side 108 and the palmar side 110 of the glove body 102 between the thumb portion 114 and the wrist portion 112 of the glove 100. For example, the opening 138 of the cut out portion 126 may be manufactured by removing substantially the same amount of material from the reinforcing panel 124 on substantially both sides of the longitudinal axis 800 which runs substantially along the boundary between the dorsal side 108 and the palmar side 110 of the glove body 102. In other words, the opening 138 of the cut out portion 126 defines a void where the material from the glove body 102 and/or reinforcing panel 124 has been removed during manufacture as shall be discussed in greater detail below.

Referring back to FIGS. 2 and 4, the cut out portion 126, whether formed through the reinforcing panel 126 or directly through the glove body 102 may be manufactured using the following dimensions. In some embodiments, opening 138 of the cut out portion 126 may have a length 900 of about 40 mm, a depth 902 of about 15 mm, and a width 904 of about 30 mm. The apparatus, methods, and articles of manufacture are not limited in this regard.

Figure 8:
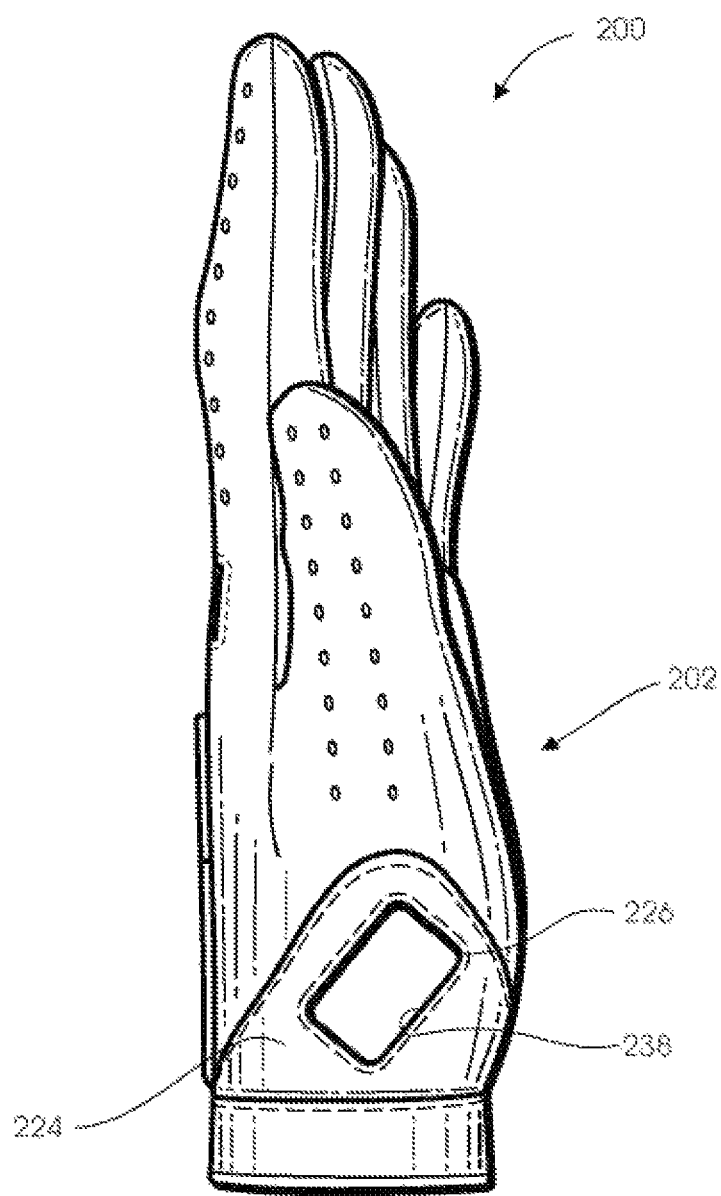
FIG. 8 is a side view of an embodiment of a glove illustrating a cut out portion having a substantially rectangular-shaped configuration.
Figure 9:
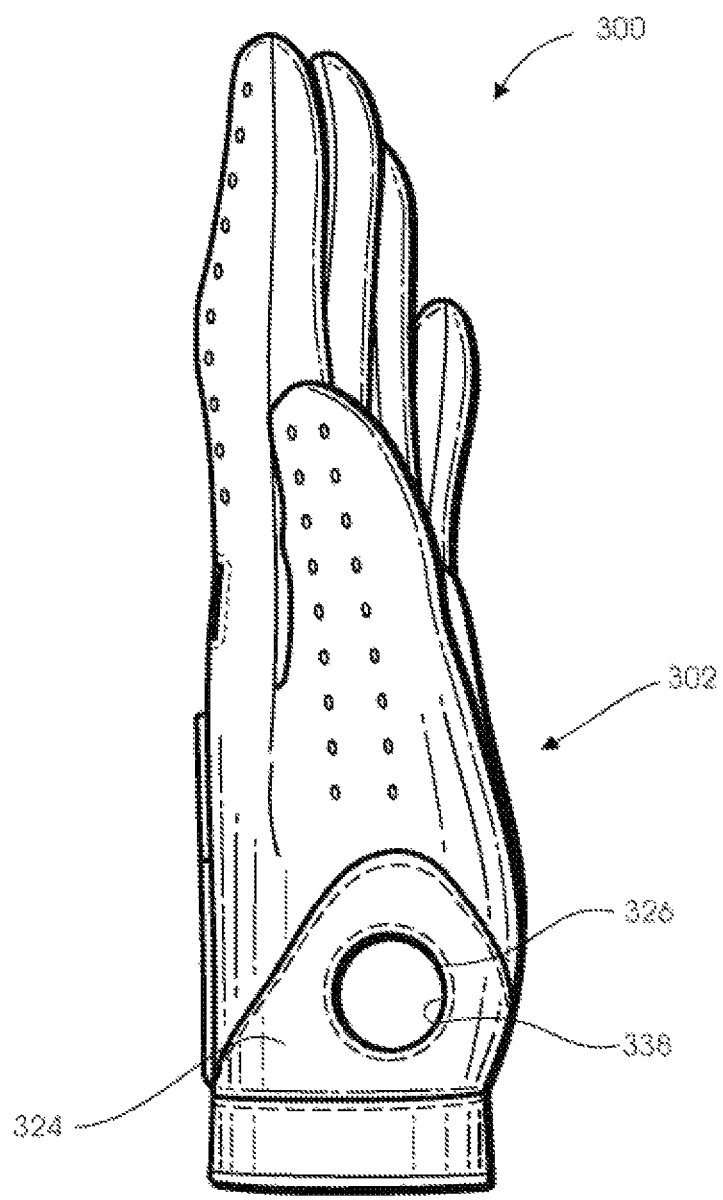
FIG. 9 is a side view of an embodiment of a glove illustrating a cut out portion having a substantially circular-shaped configuration.
Figure 10:
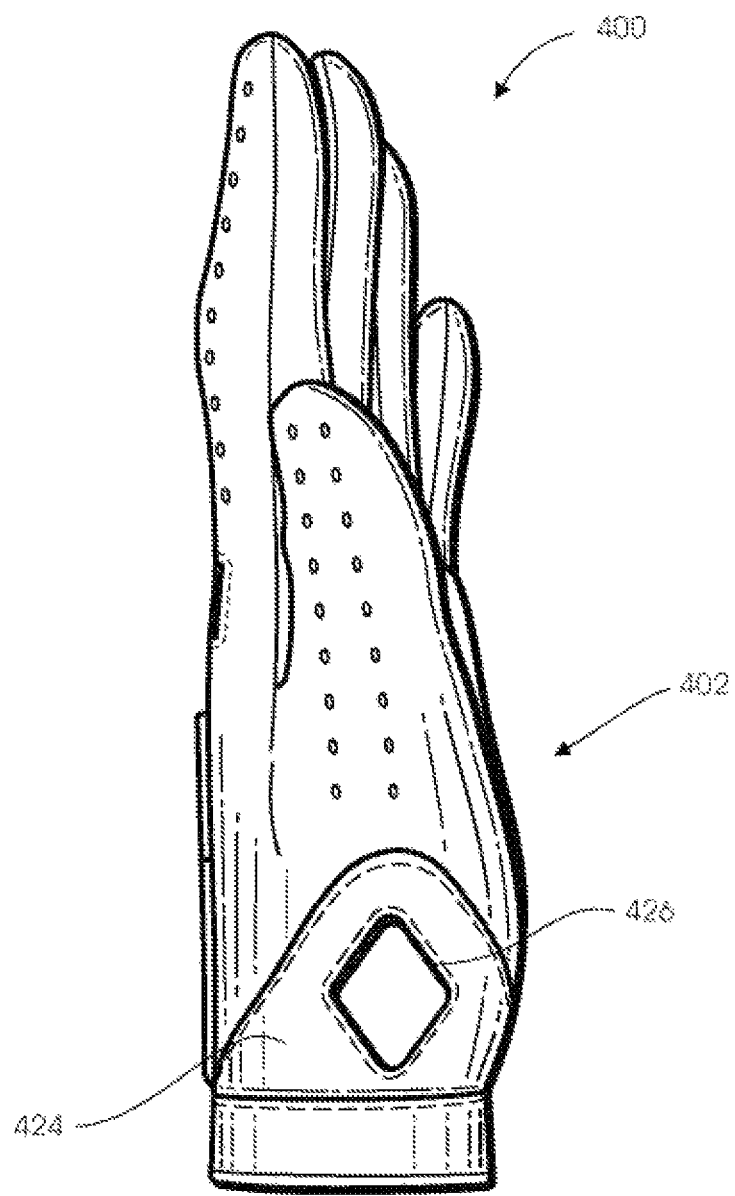
FIG. 10 is a side view of an embodiment of a glove illustrating a cut out portion having a substantially diamond-shaped configuration.
Figure 11:
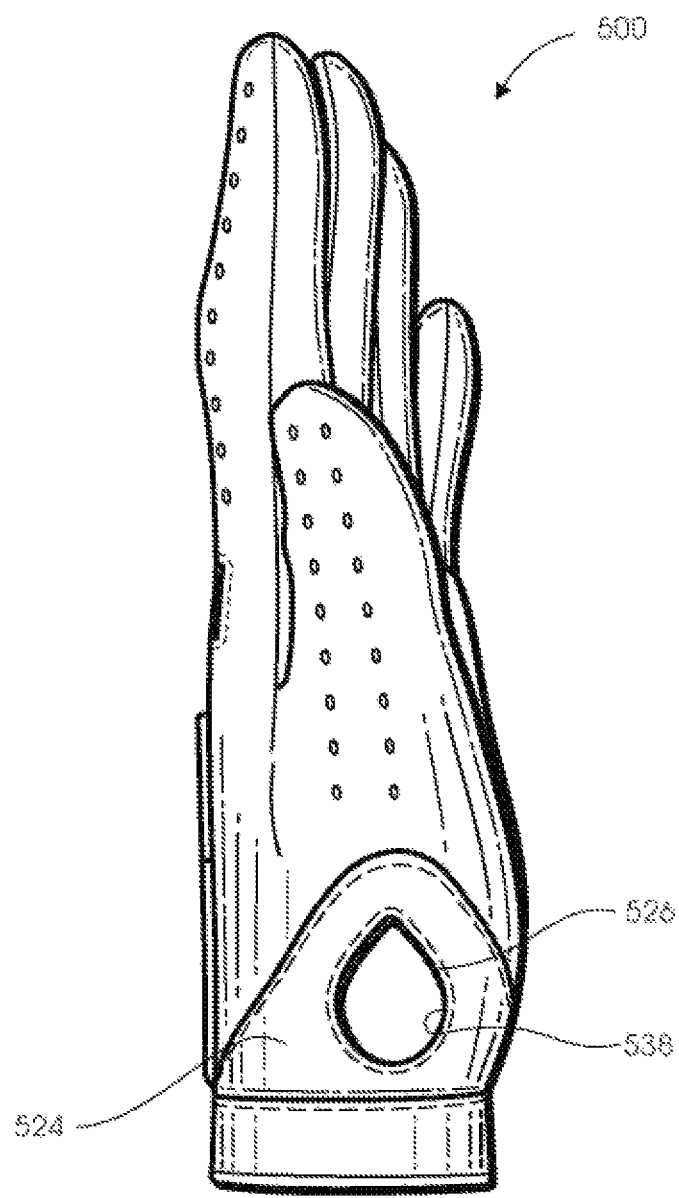
FIG. 11 is a side view of an embodiment of a glove illustrating a cut out portion having a substantially tear-drop-shaped configuration.

Referring to FIGS. 7-11, the reinforcing panel 124 may have a cut out portion 126 defining an opening with different symmetrical configurations. For example, as shown in FIG. 7, glove 100 includes a glove body 102 having a reinforcing panel 124 forming an opening 138 that defines a substantially symmetrical oval-shaped configuration. In FIG. 8 another embodiment of a glove, designated 200, may include a glove body 202 having a reinforcing panel 224 that defines a cut out portion 226 with an opening 238 forming a substantially symmetrical rectangular-shaped configuration. Referring to FIG. 9, in another embodiment of a glove, designated 300, may include a glove body 302 having a reinforcing panel 324 with a cut out portion 326 that defines an opening 338 forming a substantially symmetrical circular-shaped configuration. Referring to FIG. 10, in yet another embodiment of a glove, designated 400, may include a glove body 402 having a reinforcing panel 424 with a cut out portion 426 that defines an opening 438 forming a substantially symmetrical diamond-shaped configuration. As shown in FIG. 11, in another embodiment of a glove, designated 500, may include a glove body 502 having a reinforcing panel 524 with a cut out portion 526 that defines an opening 538 forming a substantially symmetrical tear-drop-shaped configuration. Regardless of the symmetrical configuration of the openings 138, 238, 338, 438, and 538, each opening 138, 238, 338, 438, and 538 is formed such that substantially half the opening 138, 238, 338, 438, and 538 is formed on the dorsal side 108 of the glove body 102, while the other half of the opening 138, 238, 338, 438 and 538 is formed along the palmar side 110 of the glove body 102. In this configuration of the opening 138, 238, 338, 438, and 538, the stress forces generated when the individual hinges the wrist are distributed substantially equally along the opening 138, 238, 338, 438, and 538, thereby substantially preventing the bunching up of glove material 103. While the examples may describe particular configurations for openings 138, 238, 338, 438, and 538, the apparatus, methods, and articles of manufacture described herein are not limited in this regard.

Figure 6:
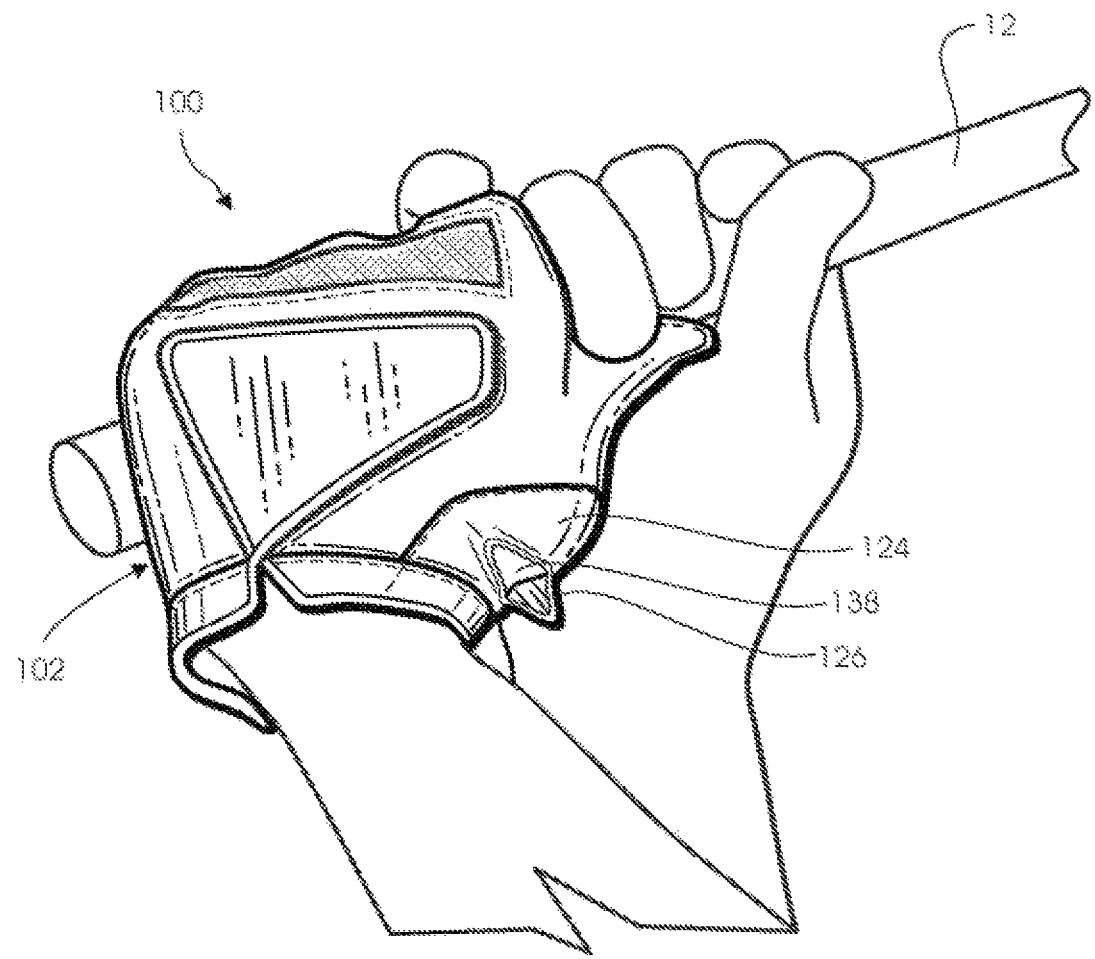
FIG. 6 is a perspective view of the glove of FIG. 1 being worn by an individual showing that the cut out portion prevents bunching up of glove material.

Referring back to FIGS. 1 and 2, in some embodiments the dorsal side 108 of the glove body 102 may include a flexible portion 136. For example, a flexible portion 136 may be located proximate the plurality of finger portions 115 formed substantially on the dorsal side 108 of the glove body 102, although the flexible portion 136 may be located along other areas of the glove body 102. In this location, the flexible portion 136 provides a flexible zone in the glove material 103 of the glove body 102 adjacent an individual's knuckles to provide additional flexibility when the glove 100 is worn by an individual as shown in FIG. 6. While one embodiment depicts the flexible portion 136 proximate the plurality of finger portions 115, the apparatus, methods, and articles of manufacture described herein are not limited in this regard.

As shown in FIG. 2, the dorsal side 108 of the glove body 102 may define a dorsal portion 113 proximate the plurality of finger portions 115, the thumb portion 114 and the wrist portion 112 of the glove body 102. In addition, the dorsal portion 113 may form a first engagement portion 140 configured to engage a second engagement portion 142 when an individual is putting on the glove 100. In some embodiments, the first engagement portion 140 includes a first VELCRO® hook and loop arrangement 143, such as configured to engage a second VELCRO® hook and loop arrangement portion 144 on the second engagement portion 142 that permits the first engagement portion 140 to be repeatedly attached and detached from the second engagement portion 142 when an individual wishes to pull on or off the glove 100.

Referring to FIGS. 1 and 2, in some embodiments, the glove 100 may define a plurality of holes 132 formed through portions of the glove body 102, such as the plurality of finger portions 115 and the thumb portion 114 to provide air circulation to an individual's hand and permit moisture from the hand to escape through the glove material 103. In some embodiments, the plurality of holes 132 may be defined along any suitable area on the dorsal portion 113 and/or the palmar portion 111 (FIG. 3) of the glove body 102. The apparatus, methods, and articles of manufacture are not limited in this regard.

Referring back to FIG. 4, as noted above, an individual may use the cut out portion 126 of the reinforcing panel 124 to more effectively pull the glove 100 over the individual's hand. In particular, the opening 138 of the cut out portion 126 is configured to allow an individual to insert one or more fingers through the opening 138 and into the interior portion 130 of the glove 100. The individual may then apply a downward force 146 with the finger(s) of one hand against the surface of the cut out portion 126 to facilitate insertion of the individual's other hand into the interior portion 130 through the wrist portion 112 such that the fingers and thumb of the individual's other hand can be easily inserted into the plurality of finger portions 115 and the thumb portion 114 of the glove body 102, respectively, without the individual having to directly grasp the wrist portion 112 or unduly wriggle or manipulate the individual's other hand to insert the hand into the glove 100.

Figure 5:
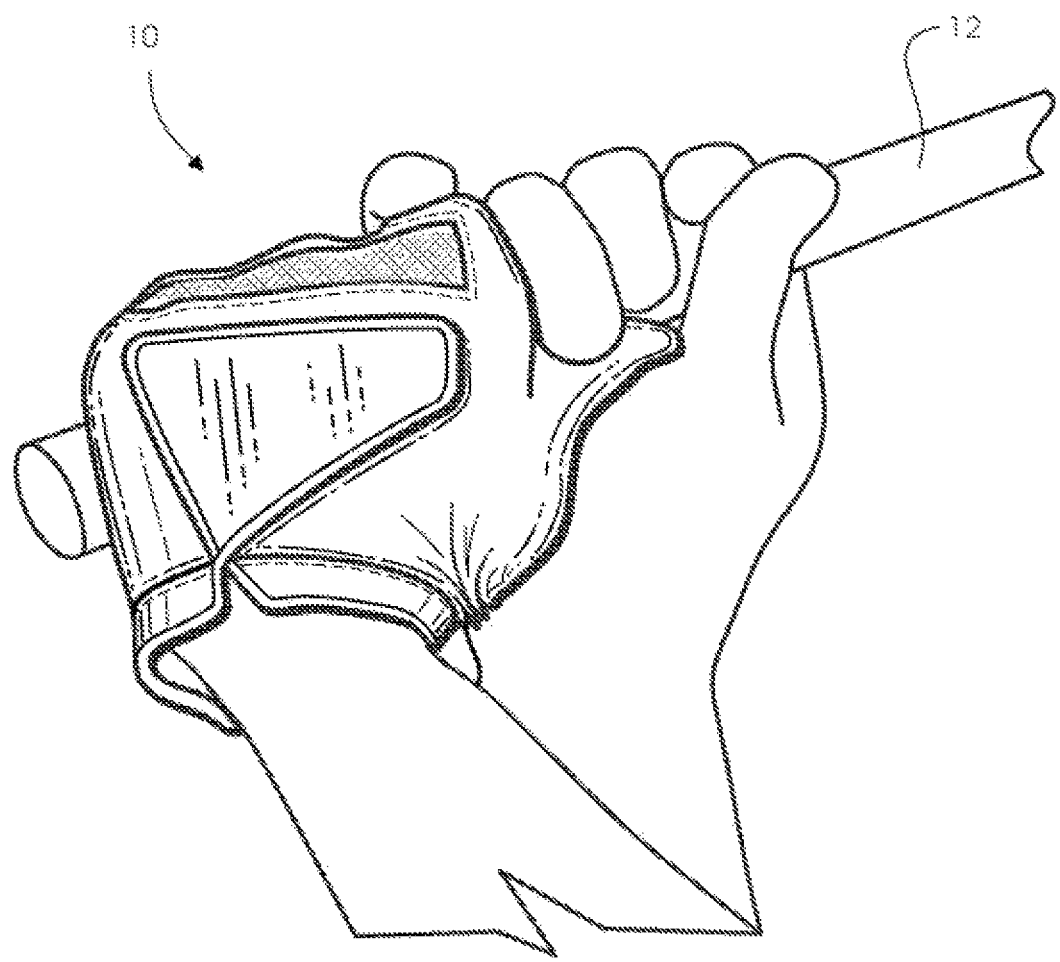
FIG. 5 is a perspective view of a prior art glove being worn by an individual showing the bunching up of glove material that can occur when grasping an article.

In one aspect shown in FIG. 6, the cut out panel 124 of the reinforcing panel 124 prevents the bunching up of the glove material 103 that can occur when an individual is in the act of swinging a golf club 12. As shown in FIG. 5, the glove material of a prior art glove 10 can tend to "bunch up" when an individual has his or her wrist hinged back relative to the forearm of an individual when swinging the golf club 12. This bunching up of the prior art glove 10 occurs because the hinging back of the wrist naturally causes the glove material of the prior art glove 10 to naturally "bunch up" or gather together substantially between the wrist portion and the thumb portion of the prior art glove 10. In addition, this bunching up of the prior art glove 10 may be undesirable since it can cause discomfort to the individual and/or distract the individual during the golf swing. Referring to FIG. 6, in contrast to the prior art glove 10, the glove 100 includes the opening 138 of the cut out portion 126 that substantially minimizes or eliminates the bunching up of the glove body 102, for example, when the wrist of an individual is hinged during a golf swing. In particular, the bunching up of the glove 100 is substantially minimized or eliminated since the opening 138 defined by the cut out portion 126 forms a void from the removed glove material 103 that would otherwise bunch up in a prior art glove 10 when an individual hinges the wrist. In addition, the opening 138 deforms when an individual hinges the wrist, thereby further preventing the glove material 103 from bunching up together.

Figure 12:
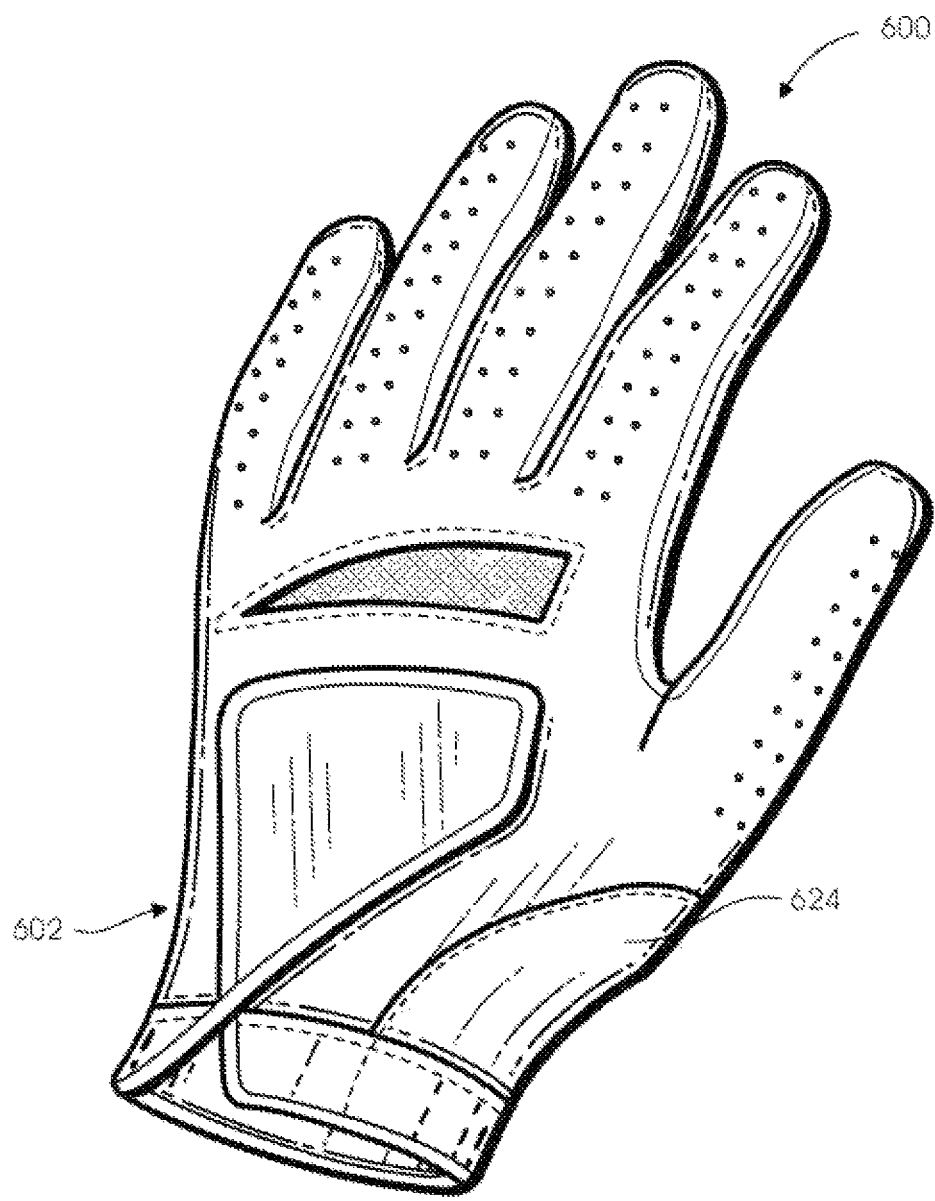
FIG. 12 is a perspective view of an embodiment of a glove showing a reinforcing portion.

Referring to FIG. 12, in one embodiment of a glove, designated 600, may include a glove body 602 having a reinforcing panel 624 without any cut out portion for substantially preventing the formation of any failure zones in the glove body 602 that can develop after repeated use of a glove. In particular, the reinforcing panel 624 is made from a resilient, durable and wear-resistant material that substantially reduces the chances of the glove 100 developing a failure zone when the individual applies stress to the glove body 102 while pulling the glove 100 onto or off of the hand of an individual.

Figure 13:
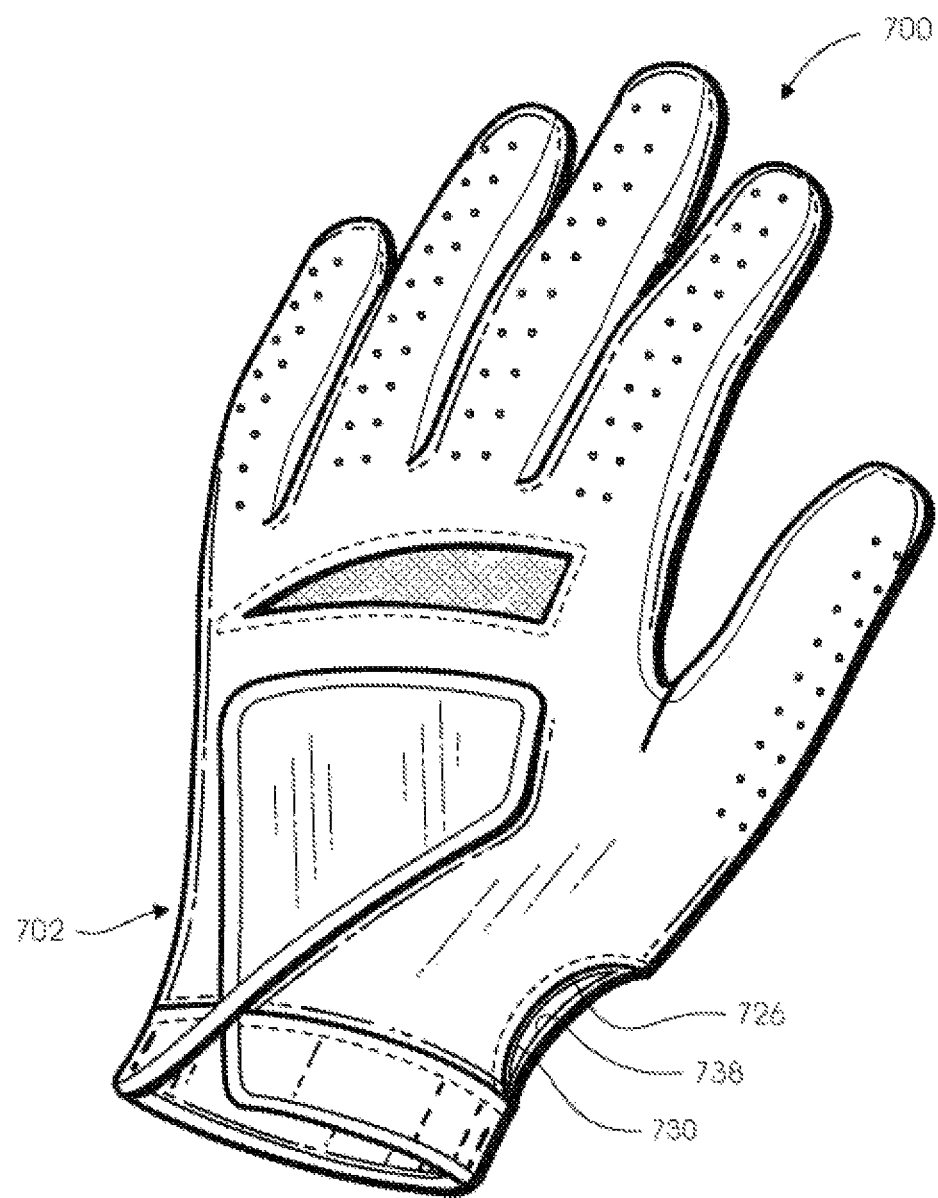
FIG. 13 is a perspective view of an embodiment of a glove showing a cut out portion defining an opening.

Referring to FIG. 13, in one embodiment of the glove, designated 700, may include a cut out portion 726 that is formed directly through the glove body 702. In this embodiment, the cut out portion 726 does not form a part of any kind of reinforcing panel as discussed above, but is formed directly through the glove body 702. As shown, the cut out portion 726 forms an opening 738 in direct communication with an interior portion 730 defined by the glove body 702. Similar to the embodiments of gloves 100, 200, 300, 400, and 500 having respective cut out portions 126, 226, 326, 426, and 526, the cut out portion 726 of glove 700 is configured to function in substantially the same manner in that an individual may insert one or more fingers through the opening 738 and apply a downward force against the cut out portion 726 to assist in pulling the glove 700 onto the hand in a more effective manner as illustrated in FIG. 4.

Figure 15:
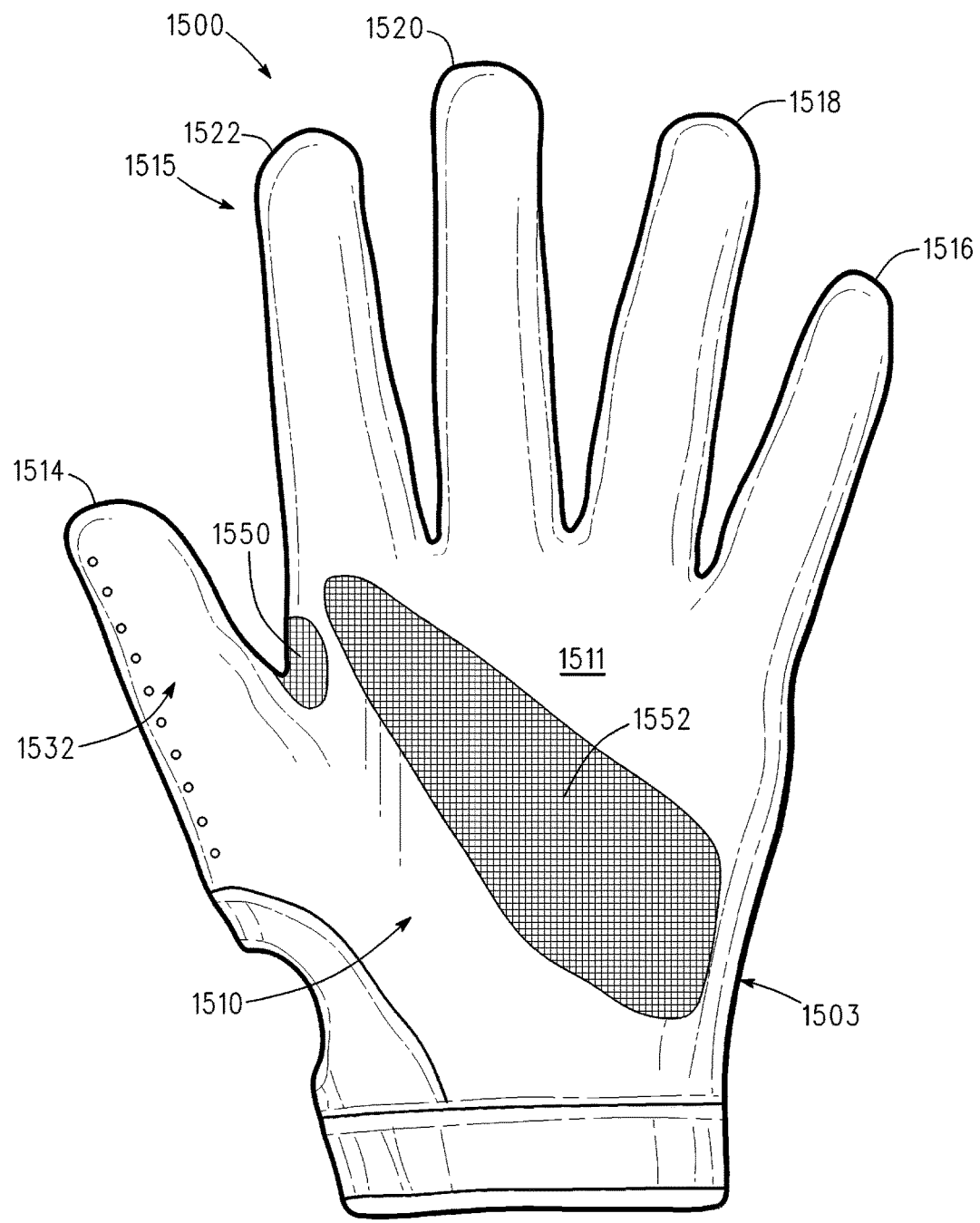
FIG. 15 is a rear view of an embodiment of a glove showing a flexible panel on the palmer side of the glove.

Another embodiment of the glove 1500, shown in FIG. 15, may further include a panel 1552 comprising a lightweight, flexible and permeable material on the palmar side 1510 of the glove 1500. The lightweight, flexible and permeable panel 1552 replaces a portion of the glove material 1503. The lightweight, flexible and permeable panel 1552 is inserted in the palm portion 1511 on the palmar side 1510 of the glove 1500. The lightweight, flexible and permeable panel 1552 extends from the base of the fourth finger portion 1522 to the bottom of the palm portion 1511 opposite the base of the thumb portion 1514. In other embodiments, the panel 1552 can extend from any of the plurality of finger portions 1515 (e.g. the first finger portion 1516, the second finger portion 1518, the third finger portion 1520, or the fourth finger portion 1522).

A width 1590 of the lightweight, flexible and permeable panel 1552 can vary. In some embodiment, the width 1590 of the panel 1552 can increase from near the base of the fourth finger portion 1522 toward the bottom of the palm 1511; while in other embodiments, the width 1590 of the panel 1552 can decrease from near the base of the fourth finger portion 1522 toward the bottom of the palm 1511. Still in other embodiments, the width 1590 of the panel 1552 can increase and/or decrease in any variation from near the base of the fourth finger portion 1522 toward the bottom of the palm 1511. In the illustrated embodiment, the width 1590 of the panel 1552 is smallest at or near the base of the fourth finger portion 1522 and widest at or near the bottom of the palm portion 1511 opposite the base of the thumb portion 1514. Feel, breathability, and grip strength are improved and glove weight is reduced by using a lightweight, flexible and permeable type material for the panel. In addition, the lightweight, flexible and permeable panel in the palm portion 1511 improves the fit of the glove, as the panel 1552 allows the glove 1500 to expand and fit the golfer's hand more easily than the rest of the glove material 1503.

In some embodiments, the glove 1500 includes another lightweight, flexible and permeable panel 1551 between the base of thumb portion 1514 and the base of the fourth finger portion 1522. In these or other embodiments, the lightweight, flexible and permeable panel 1551 prevents the bunching of material between the base of the thumb portion 1514 and the base of the fourth finger portion 1522 when the player is grasping the grip of the golf club. In many embodiments, the lightweight, flexible and permeable panels 1550, 1551 comprises a mesh material such as polyester mesh, mesh netting, tulle, power mesh, or nylon mesh. In other embodiments, the panels 1550, 1551 can comprise other materials such as polyester, chiffon, spandex, or any other lightweight, flexible and permeable material. In other embodiments, the flexible panels 1550, 1551 may comprise any other suitable material.

Figure 14:
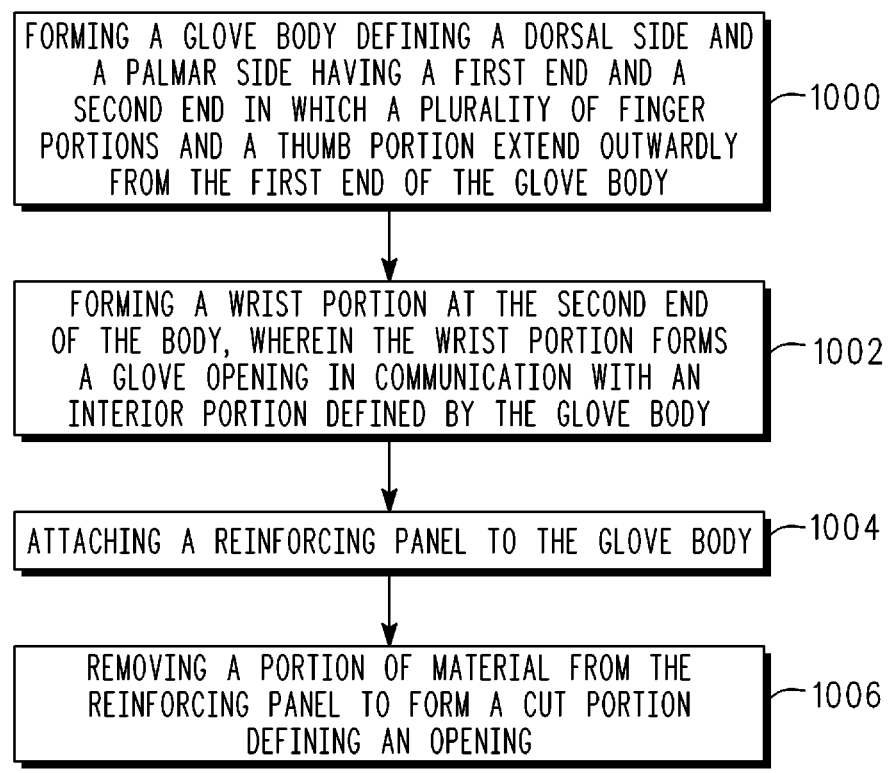
FIG. 14 is a flow chart illustrating one method of manufacturing the glove of FIG. 1.

Referring to FIG. 14, one method for manufacturing the glove 100 is illustrated. At block 1000, forming the glove body 102 defining a dorsal side 108 and a palmar side 110 having a first end 104 and a second end 106, wherein a plurality of finger portions 115 and a thumb portion 114 extend outwardly from the first end 104 of the glove body 102. At block 1002, forming a wrist portion 112 at the second end 106 of the glove body 102, wherein the wrist portion 112 forms a glove opening 128 in communication with an interior portion 130 defined by the glove body 102. In block 1004, attaching a reinforcing panel 124 to the glove body 102 such as by sewing the reinforcing panel 124 to the glove body 102. At block 1006, removing a portion of the material from the reinforcing panel 124, such as by cutting a portion of the glove material 103 away, to form a cut out portion 126 defining an opening 138.

While a particular order of actions is illustrated in FIG. 14, these actions may be performed in other temporal sequences. For example, two or more actions depicted in FIG. 14 may be performed sequentially, concurrently, or simultaneously. Alternatively, two or more actions depicted may be performed in reverse order. Furthermore, one or more actions in FIG. 14 may not be performed at all. The apparatus, methods, and articles of manufacture described herein are not limited in this regard.

In some embodiments, gloves 100, 200, 300, 400, 500, 600 and 700 may be a golf glove, a racing glove, a gardening glove, a kitchen glove, a mitten glove, a disposable glove, a fingerless glove, a cycling glove, a boxing glove, a handler's glove, a welder's glove, an impact protection glove, a food service glove, a chainmail glove, a chainsaw glove, a fireman's gauntlet, an archer's glove, a baseball glove, an ice hockey glove, a riding glove, a lacrosse glove, a fencing glove, a cricket glove, a billiards glove, a falconry glove, a weightlifting glove, a ski glove, a touchscreen glove, and a wheelchair glove.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A glove comprising:
    a glove body comprising:
        a dorsal side and a palmar side having a first end and a second end;
        a plurality of finger portions and a thumb portion extending from the first end; and
        a wrist portion defined at the second end, wherein the wrist portion defines a glove opening in communication with an interior portion defined within the glove body;
        a reinforcing panel secured on an outer surface of the glove body between the thumb portion and the wrist portion;
        a cut out portion defining an opening formed through the reinforcing panel and in communication with the interior portion of the glove body to minimize bunching up of the glove body; and one or more panels comprising a material selected from the group consisting of polyester, nylon, leather, chiffon, spandex, and combinations thereof.

2. The glove of claim 1, wherein the cut out portion prevents bunching up of the glove body in an area of the glove body.

3. The glove of claim 1, wherein the cut out portion prevents bunching up of the glove body in an area of the glove body between the thumb portion and the wrist portion.

4. The glove of claim 1, wherein the opening of the cut out portion is formed through the dorsal side and the palmar side of the glove body.

5. The glove of claim 1, wherein the opening of the cut out portion is formed through the dorsal side and the palmar side of the glove body such that substantially equal amounts of the glove material are formed through the dorsal side and palmar side of the glove body.

6. The glove of claim 1, wherein the opening of the cut out portion comprises at least one of a substantially oval-shaped configuration, a substantially circular-shaped configuration, a substantially rectangular-shaped configuration, or a substantially tear-drop-shaped configuration.

7. The glove of claim 1, wherein the reinforcing panel comprises at least one of a leather material, a flexible soft touch polymer material, a woven material, or a variety of synthetic textile materials.

8. The glove of claim 1, wherein the cut out portion is formed in a portion of the glove body where a material of the glove body has been removed to create a void that prevents the portion of the glove body from bunching up.

9. The glove of claim 1, wherein the opening of the cut out portion is symmetrical in configuration about a longitudinal axis, wherein the longitudinal axis extends along a boundary between the dorsal side and palmar side of the glove body.

10. The glove of claim 1, wherein the glove is a golf glove, a racing glove, a gardening glove, a kitchen glove, a mitten glove, a disposable glove, a fingerless glove, a cycling glove, a boxing glove, a handler's glove, a welder's glove, an impact protection glove, a food service glove, a chainmail glove, a chainsaw glove, a fireman's gauntlet, an archer's glove, a baseball glove, an ice hockey glove, a riding glove, a lacrosse glove, a fencing glove, a cricket glove, a billiards glove, a falconry glove, a weightlifting glove, a ski glove, a touchscreen glove, or a wheelchair glove.

11. The glove of claim 1, wherein one panel of the one or more panels is positioned on the palmar side of the glove.

12. The glove of claim 1, wherein one panel of the one or more panels is positioned between the thumb portion and a fourth finger portion.

13. A glove comprising:
    a glove body comprising:
        a dorsal side and a palmar side having a first end and a second end;
        a plurality of finger portions and a thumb portion extending from the first end;
        a wrist portion defined at the second end, wherein the wrist portion defines a glove opening in communication with an interior portion defined within the glove body;
        a cut out portion defining an opening formed through the glove body and in communication with the interior portion of the glove body to minimize bunching up of the glove body; and one or more panels comprising a material selected from the group consisting of polyester, nylon, leather, chiffon, spandex, and combinations thereof.

14. The glove of claim 13, wherein the opening of the cut out portion is symmetrical in configuration about a longitudinal axis, wherein the longitudinal axis extends along a boundary between the dorsal side and palmar side of the glove body.

15. The glove of claim 13, wherein the glove is a golf glove, a racing glove, a gardening glove, a kitchen glove, a mitten glove, a disposable glove, a fingerless glove, a cycling glove, a boxing glove, a handler's glove, a welder's glove, an impact protection glove, a food service glove, a chainmail glove, a chainsaw glove, a fireman's gauntlet, an archer's glove, a baseball glove, an ice hockey glove, a riding glove, a lacrosse glove, a fencing glove, a cricket glove, a billiards glove, a falconry glove, a weightlifting glove, a ski glove, a touchscreen glove, or a wheelchair glove.

16. The glove of claim 13, wherein one panel of the one or more panels is positioned on the palmar side of the glove.

17. The glove of claim 13, wherein one panel of the one or more panels is positioned between the thumb portion and a fourth finger portion.

\* \* \* \* \*